US011844704B2

(12) United States Patent
Garvey et al.

(10) Patent No.: US 11,844,704 B2
(45) Date of Patent: Dec. 19, 2023

(54) INSTRUMENTS AND METHOD FOR ANKLE REPLACEMENT SURGERY

(71) Applicant: restor3d, Inc., Durham, NC (US)

(72) Inventors: Brian Garvey, Bryn Mawr, PA (US); Deepak Padmanabhan, Philadelphia, PA (US)

(73) Assignee: RESTOR3D, INC., Durham, NC (US)

( * ) Notice: Subject to any disclaimer, the term of this patent is extended or adjusted under 35 U.S.C. 154(b) by 464 days.

(21) Appl. No.: 17/025,151

(22) Filed: Sep. 18, 2020

(65) Prior Publication Data

US 2021/0077276 A1 Mar. 18, 2021

Related U.S. Application Data

(60) Provisional application No. 62/902,181, filed on Sep. 18, 2019.

(51) Int. Cl.
*A61F 2/46* (2006.01)
*A61F 2/30* (2006.01)

(52) U.S. Cl.
CPC .... *A61F 2/4606* (2013.01); *A61F 2002/3054* (2013.01); *A61F 2002/30433* (2013.01); *A61F 2002/4627* (2013.01); *A61F 2002/4687* (2013.01)

(58) Field of Classification Search
CPC . A61B 17/1775; A61B 17/8897; A61B 90/11; A61B 2090/701; A61B 1/005; A61B 1/0051; A61B 1/008; A61B 1/012; A61B 17/6425; A61B 17/6458; A61B 17/6466; A61B 17/6475; A61B 17/6483; A61B 17/6491; A61F 2/4606; A61F 2002/4627; A61F 2002/4628; A61F 2002/4687
See application file for complete search history.

(56) References Cited

U.S. PATENT DOCUMENTS

| | | | | |
|---|---|---|---|---|
| 6,461,358 B1 * | 10/2002 | Faccioli | ............. | A61B 17/6425 606/57 |
| 8,382,755 B2 * | 2/2013 | Austin | ............... | A61B 17/6416 606/54 |
| 2007/0100346 A1 * | 5/2007 | Wyss | ..................... | A61B 90/50 606/87 |

* cited by examiner

*Primary Examiner* — Anu Ramana
(74) *Attorney, Agent, or Firm* — Husch Blackwell LLP; Bryan D. Stewart; Andrew C. Landsman

(57) ABSTRACT

The present disclosure generally discloses instruments and methods of using those instruments for performing various aspects of ankle replacement surgery. In one embodiment, an alignment assembly for adjusting a position of a guide tool relative to a patient is provided. The alignment assembly includes a proximal housing; a distal housing configured to be connected to the guide tool; and at least one linkage system configured to adjust a relative angle between at least two portions of the alignment assembly. A surgical guide wire is also disclosed. The surgical guide wire includes a distal tip having a tapered or trocar end configured for insertion into a bone; a distal region adjacent to the distal tip; a transition region adjacent to the distal region; and a proximal region adjacent to the transition region.

12 Claims, 16 Drawing Sheets

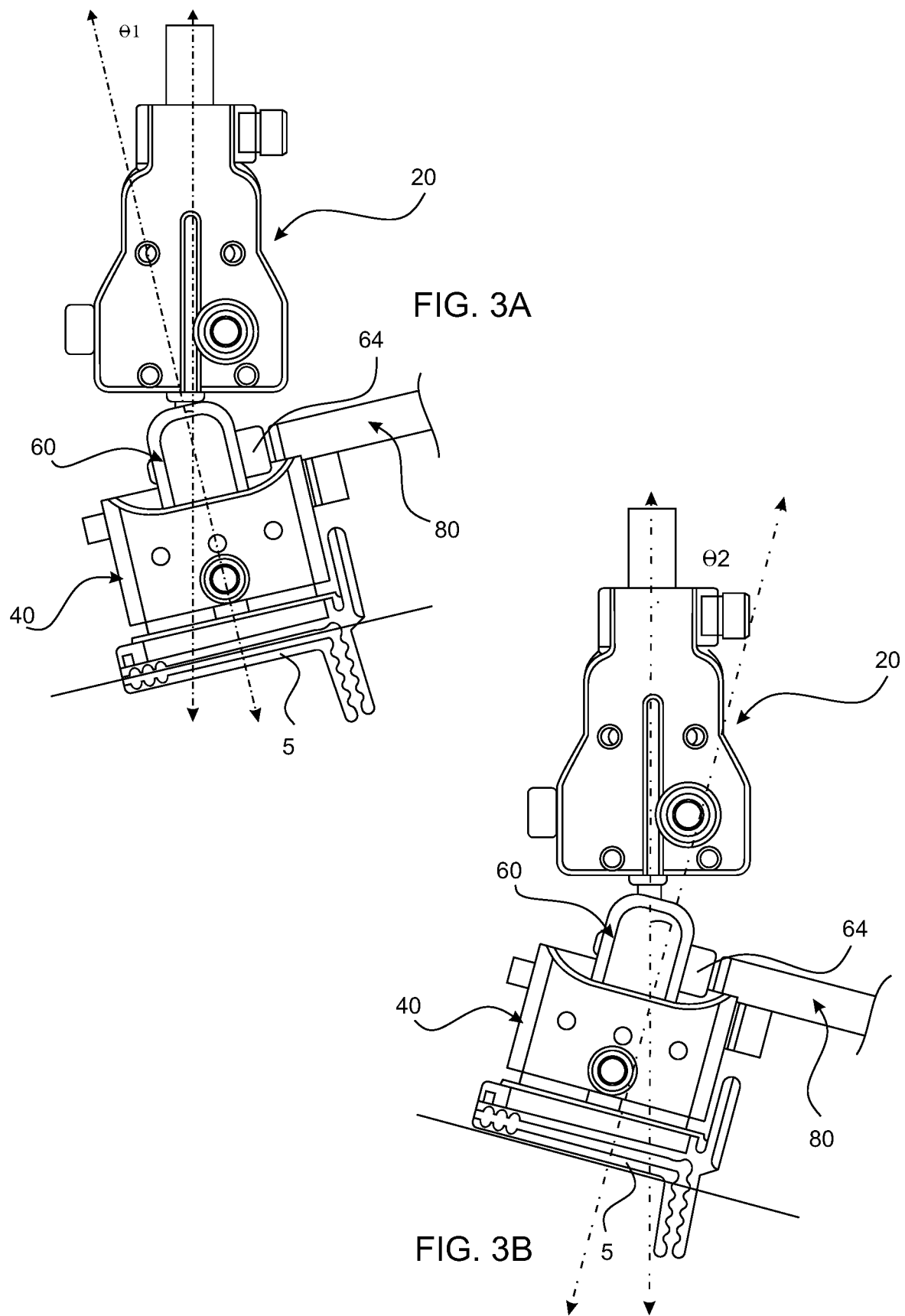

INSTRUMENTS AND METHOD FOR ANKLE REPLACEMENT SURGERY

INCORPORATION BY REFERENCE

The following document is incorporated in its entirety by reference as if fully set forth herein: U.S. Provisional Patent Application 62/902,181, filed Sep. 18, 2019.

FIELD OF INVENTION

The present disclosure relates to tools and methods for performing ankle replacement surgery.

BACKGROUND

Ankle replacement surgery is a procedure for treating patients with end stage ankle arthritis, rheumatoid arthritis and other painfully arthritic conditions of the ankle or other maladies. Total ankle replacement (TAR), as it is commonly referred to, is typically not as clinically successful as other total joint replacements (i.e. knee, hip, shoulder). The failure rates of TAR procedures are sometimes two or three times greater than total knee or total hip replacement.

One of the more difficult aspects of a TAR procedure is manually aligning the patient's ankle joint so that the surgeon may make the appropriate bone resection cuts. The location and accuracy of the bone resection cuts determine the location of the total ankle implant and ultimately determine how well the implant will function and to what extent the patient's quality of life has improved. Accordingly, making accurate incisions is critical to a successful surgery and recovery.

The ankle joint must be appropriately aligned with long axis of the tibial bone in order to place the implant where it will most effectively provide the requisite range of motion and counteract the forces experienced in daily activities, such as walking, jogging, standing, etc. There are six degrees of freedom that must be aligned by the surgeon during the surgery. The alignment of the ankle joint is achieved with instruments used to prepare the tibial and talar bones in preparation of implant placement.

It would be desirable to provide instruments and tools that ensure surgeons and other medical personnel can perform reliable and accurate alignment of a patient's ankle joint prior to and during surgery.

SUMMARY

The present disclosure generally discloses instruments and methods of using those instruments for performing various aspects of ankle replacement surgery.

In one embodiment, an instrument and method of adjusting two degrees of freedom is provided. The instrument contains a linkage that is positioned specifically to allow the surgeon to adjust varus and valgus angular position of the instrument relative to the patient's anatomy. In one embodiment, these adjustments are made between +75° and −75° from a line perpendicular to a longitudinal axis of the tibial bone.

In one embodiment, another linkage and method of using the linkage is provided. The linkage is positioned specifically to allow the surgeon to adjust the opening angle (commonly referred to as "slope") of the instrument relative to the patient's anatomy. In one embodiment, both of these linkages utilize a screw or gear type feature that actuates the adjustment assembly, causing rotation about a fixed point, thereby adjusting the relative angle between the instrument and the bone. In one embodiment, these adjustments are made between +45° and −45° from a line perpendicular to the long axis of the tibial instrument. The alignment guide permits these adjustments and reduces the likelihood of misalignment and improves a surgeon's ability to precisely select an angle most appropriate for the patient.

An alignment assembly for adjusting a position of a guide tool relative to a patient is disclosed herein. The alignment assembly includes a proximal housing; a distal housing configured to be connected to the guide tool; and at least one linkage system configured to adjust a relative angle between the proximal housing and the distal housing.

In one aspect, the at least one linkage system includes a first linkage system and a second linkage system, and the first linkage system is oriented 90 degrees relative to the second linkage system such that the first and second linkage systems provide angulation about two different axes.

In another aspect, the first linkage system and the second linkage system each translate rotational input motion to linear output motion.

The relative angle is adjusted between +75° and −75° from a neutral position defined along a line extending parallel to the longitudinal axis of the tibia.

An intermediate housing can be positioned between the proximal housing and the distal housing in one embodiment.

In one embodiment, the first angular adjustment shaft includes a first threading and extends through a first linkage shaft having a second threading configured to engage with the first threading, and rotational motion applied to the first angular adjustment shaft drives the first linkage shaft linearly along the first angular adjustment shaft such that distal housing and the proximal housing pivot relative to each other in a first angular direction. The second angular adjustment shaft includes a third threading and extends through a second linkage shaft having a fourth threading configured to engage with the third threading, and rotational motion applied to the second angular adjustment shaft drives the second linkage shaft linearly along the second angular adjustment shaft such that distal housing and the proximal housing pivot relative to each other in a second angular direction.

A height adjustment assembly can be provided to adjust a relative height between the proximal housing and the distal housing.

In one aspect, a single tool can be configured to engage the first angular adjustment shaft and the second angular adjustment shaft, and the single tool is configured to rotationally engage both the first angular adjustment shaft and the second angular adjustment shaft.

In another embodiment, a surgical guide wire is provided. The wire includes: a distal tip having a tapered or trocar end configured for insertion into a bone; a distal region adjacent to the distal tip, the distal region being configured to be partially inserted into the bone; a transition region adjacent to the distal region, the transition region including a portion with a smaller diameter than a diameter of the distal region; and a proximal region adjacent to the transition region.

In one embodiment, at least a portion of the transition region has a diameter that is less than 75% of a diameter of the distal region. In another embodiment, the transition region is positioned at least ¼-⅓ of a total length of the guide wire away from the distal tip.

The transition region can have a tapered profile, with a larger end connected to the distal region and a smaller end connected to the proximal region.

The transition region can have a uniform profile having a smaller diameter than the proximal region or the distal region, a first connection portion between the transition region and the proximal region having a first tapered profile, and a second connection portion from the transition region to the distal region having a second tapered profile. The first tapered profile can be different than the second tapered profile.

Other embodiments are disclosed herein.

BRIEF DESCRIPTION OF THE DRAWINGS

The foregoing Summary and the following Detailed Description will be better understood when read in conjunction with the appended drawings, which illustrate a preferred embodiment of the invention. In the drawings:

FIGS. 3A and 3B illustrate side views of the instrument during different states of adjustment using a first linkage.

FIG. 9A is a side view of a guide wire according to one embodiment.

DETAILED DESCRIPTION OF THE PREFERRED EMBODIMENTS

Figure 1:
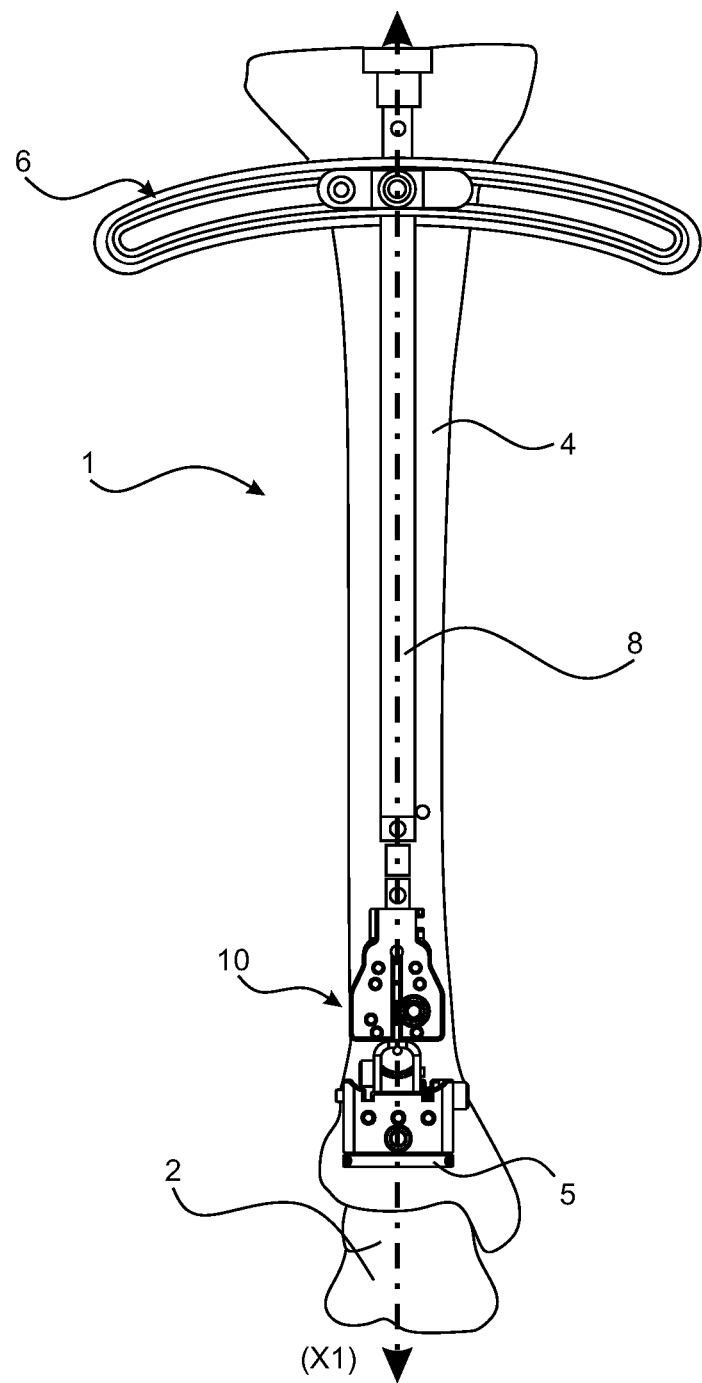
FIG. 1 is a view of an instrument according to this disclosure positioned relative to a patient's tibia and talus.

Instruments are disclosed herein that aid with adjusting the varus-valgus alignment, and adjusting the opening angle (i.e. slope) alignment. The varus-valgus adjustment is a rotational adjustment of the instruments relative to the longitudinal axis of the tibial bone when viewed in a coronal plane. This adjustment allows the surgeon to specify the coronal plane angulation of the bone cut required to place the implant, thereby specifying the coronal plane angulation of the tibial implant relative to the tibial bone. The slope adjustment is a rotational adjustment of the instruments relative to the longitudinal axis of the tibial bone when viewed in a sagittal plane. This adjustment allows the surgeon to specify the sagittal plane angulation of the bone cut required to place the tibial implant, thereby specifying the sagittal plane angulation of the tibial implant relative to the tibial bone. These instruments are intended to be used to implant any one or more of a tibial implant, a talar implant, or a bearing implant. One of ordinary skill in the art would understand that the tools can be used to align tools for other activities.

The description herein refers generally to tools and instruments for performing adjustments and alignments. One of ordinary skill in the art would understand that a corresponding method of using these tools and instruments are also within the scope of this disclosure.

In general, total ankle replacement surgery requires that a patient is placed supine on an operating table support. A protrusion or bump can be placed under the patient's calf to maintain proper rotation of the patient's leg. The patient's patella is arranged to face directly anterior. General or regional anesthesia may be used. If using regional anesthesia, the sciatic or popliteal catheter must be positioned in a way that does not interfere with the surgery. A thigh tourniquet is generally used proximal to the popliteal catheter. Intravenous antibiotics and sequential compression are used on the contralateral leg. The leg is prepared and draped using proper sterile technique, leaving the knee to foot exposed. Exsanguination is performed prior to tourniquet activation.

A skin incision is made just lateral to the tibial crest from approximately 6 cm proximal of the tibial plafond, and extending distal up to the talonavicular joint. The superficial peroneal nerve is identified and mobilized laterally. The extensor retinaculum and EHL tendon sheath are exposed, but the anterior tibial tendon sheath cannot be exposed. The deep peroneal nerve and artery are then identified and mobilized laterally. It is important to protect these structures throughout the procedure. Finally, the ankle joint capsule is incised longitudinally and exposed from the medial malleolus to the syndesmosis. Osteophytes on the neck of the talus and anterior tibia must be removed. It is important to avoid weakening the underlying bone by removing too much substrate. If a varus deformity requires correction, a deltoid release is performed. It is important to release the talar deltoid attachment from anterior to posterior as a single structure. As explained above, these surgeries and procedures are complicated and require that surgeons can correctly, accurately, and precisely have access to specific portions of the patient's anatomy. Accordingly, the subject matter disclosed herein provides an improved tool, process, and method of aligning surgical instruments and tools relative to a patent.

In one aspect, an instrument is generally disclosed herein for aligning a secondary tool (such as a bone manipulation guide) relative to a patient. The instrument includes a least one linkage system configured to adjust an angular alignment of the tool. This instrument is particularly configured to be used during ankle replacement surgery. In one aspect, the angular adjustments are between +75° and −75° from a neutral position (such as a line perpendicular to a longitudinal axis of the instrument). In one aspect, the linkage system comprises a rotating a shaft configured to rotate within an intermediate housing. The linkage system generally translates rotational motion to linear motion in one aspect. The intermediate housing may pivot relative to the proximal housing through a common point or pivot axis between the proximal housing and the linkage system.

The term secondary tool is used broadly herein to refer to any surgical tool. Specifically, the term secondary tool can refer to at least a bone manipulation guide, a saw cut guide, a k-wire guide, a broach guide, or drill guide.

The at least one linkage system includes two linkage systems in one embodiment. The two linkage systems are oriented 90 degrees relative to each other to provide angulation about two axes. In one embodiment, the angulation adjustments correspond to a coronal plane adjustment and a sagittal plane adjustment.

Referring to the drawings, an instrument 1 is provided for adjusting at least two of the degrees of freedom. FIG. 1 illustrates the instrument 1 relative to a patient's talus 2 and a patient's tibia 4. The instrument 1 generally includes a shaft alignment tool 6 that is configured to adjust a shaft 8 of the instrument relative to an axis of the tibia 4. A proximal end of the shaft 8 is attached to an adjustment assembly 10. The shaft 8 provides a reference of the instrument 1 that the surgeon may approximately align with the longitudinal axis of the patient's tibial bone in both the coronal and sagittal planes. In one example, the surgeon will provisionally align the shaft 8 to be parallel to the longitudinal axis of the patient's tibial bone in both the coronal and sagittal planes.

Regarding the adjustment assembly 10, this feature is generally provided to allow a surgeon to adjust angular positions of the instrument 1 relative to a patient's anatomy. In one aspect, the adjustments are varus and valgus adjustments. In one aspect, the adjustments provided by the adjustment assembly 10 are made between +75° and −75° from a line perpendicular to a longitudinal axis (X1) of the instrument 1, which is parallel to a longitudinal axis of the tibia 4.

Figure 2:
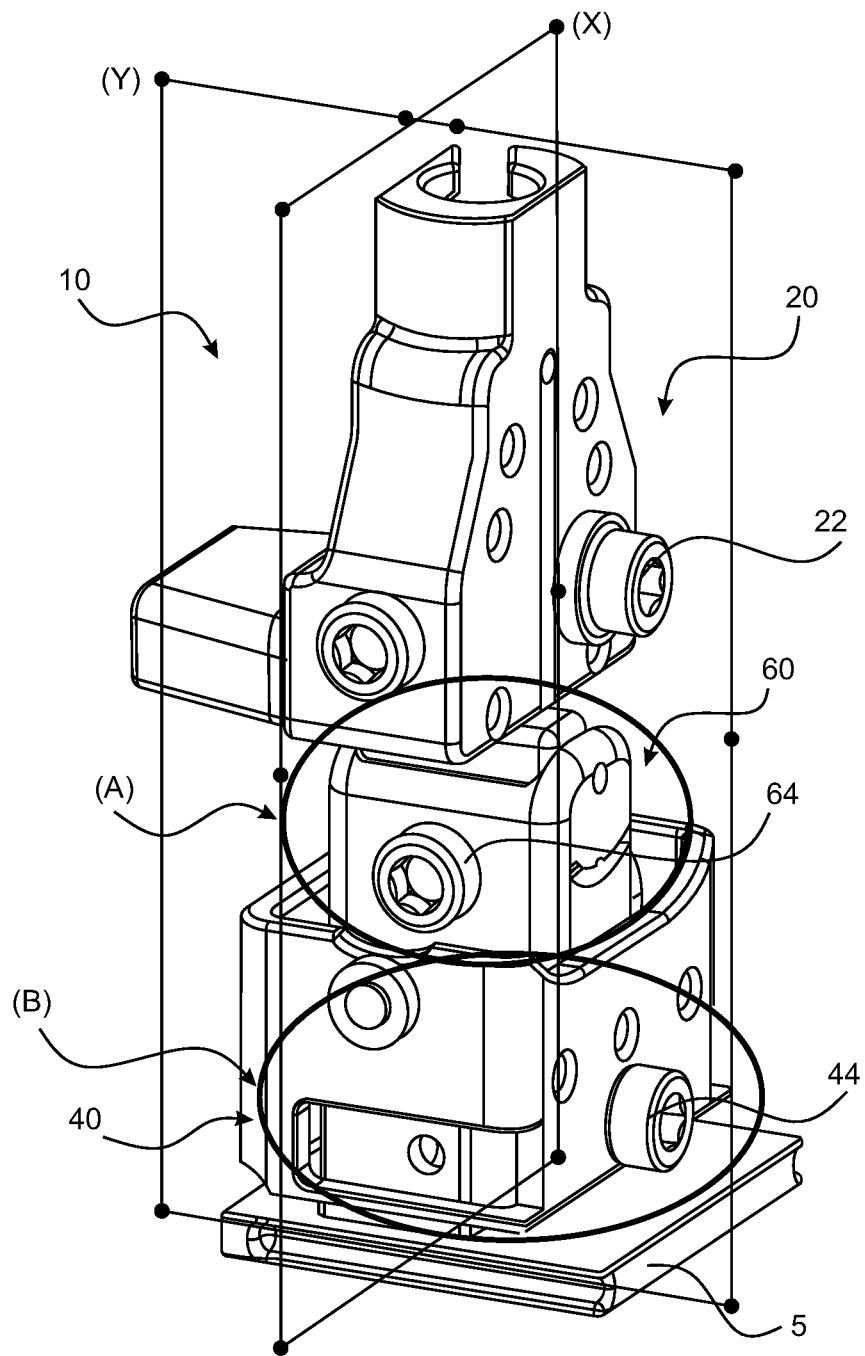
FIG. 2 is a perspective view of the instrument of FIG. 1.

The adjustment assembly 10 is shown in more detail in FIG. 2. As shown in FIG. 2, the adjustment assembly 10 includes a first or proximal housing 20 and a second or distal housing 40. At a high level, the proximal housing 20 and the distal housing 40 are adjustable relative to each other, and a carriage 45 of the distal housing 40 are adjustable relative to each other. In one aspect, the proximal housing 20 and the distal housing 40 are adjustable relative to each other via an intermediate housing 60.

Figure 4:
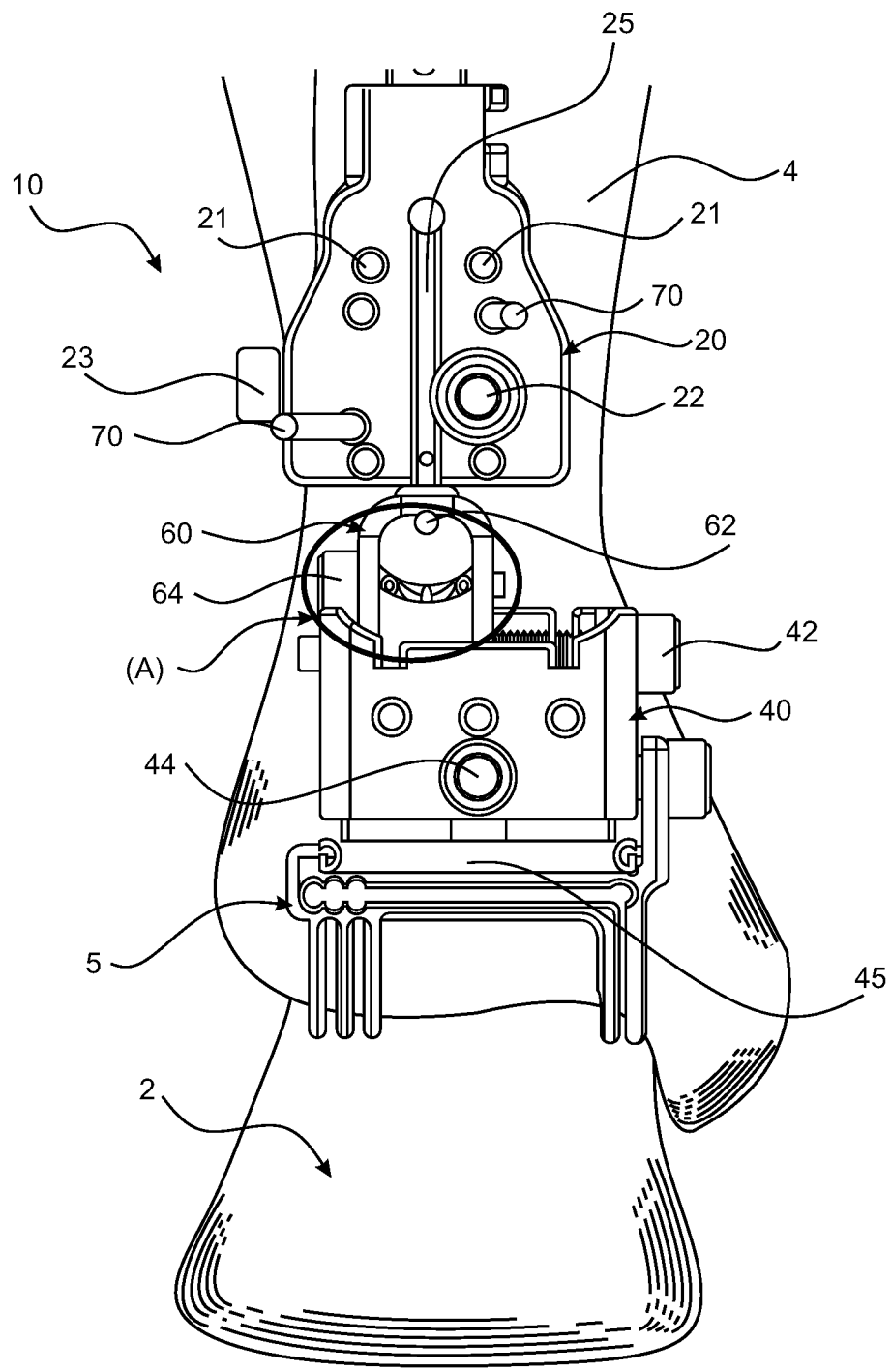
FIG. 4 is a side view of the instrument.

The proximal housing 20 includes a plurality of openings 21 which define through holes generally oriented towards the patient's anatomy. As shown in FIG. 4, at least two of the openings 21 are occupied by guide wires 70. As used herein, the term guide wires 70 generically refers to any cylindrical rod or wire that aids in attaching the instruments relative to the patient's anatomy. For example, the guide wires 70 can be a Kirschner wire or K-wire. As shown in FIG. 4, these wires 70 are generally provided to maintain alignment of the instrument and fix a position of the proximal housing 20 relative to the patient's anatomy, and more specifically relative to the tibia 4.

The proximal housing 20 can include a height adjustment assembly 22. The term height is used to refer a dimension in the longitudinal or vertical direction, i.e. the up and down direction shown in FIG. 4. The height adjustment assembly 22 can include a gear that is manually turned to adjust a relative height between the proximal housing 20 and the distal housing 40. The height can be freely adjustable in an up or down direction via the height adjustment assembly 22. Once a desired relative vertical or longitudinal distance is set between the proximal housing 20 and the distal housing 40, then a locking assembly 23 can be actuated to fix the relative distance between the proximal housing 20 and the distal housing 40. As shown in FIG. 4, an adjustment knob of the height adjustment assembly 22 is generally oriented in the same direction as the plurality of openings 21, and an axis of the locking assembly 23 is oriented perpendicular to the adjustment knob of the height adjustment assembly 22. One of ordinary skill in the art would understand that the orientation of these components can vary.

Figure 5:
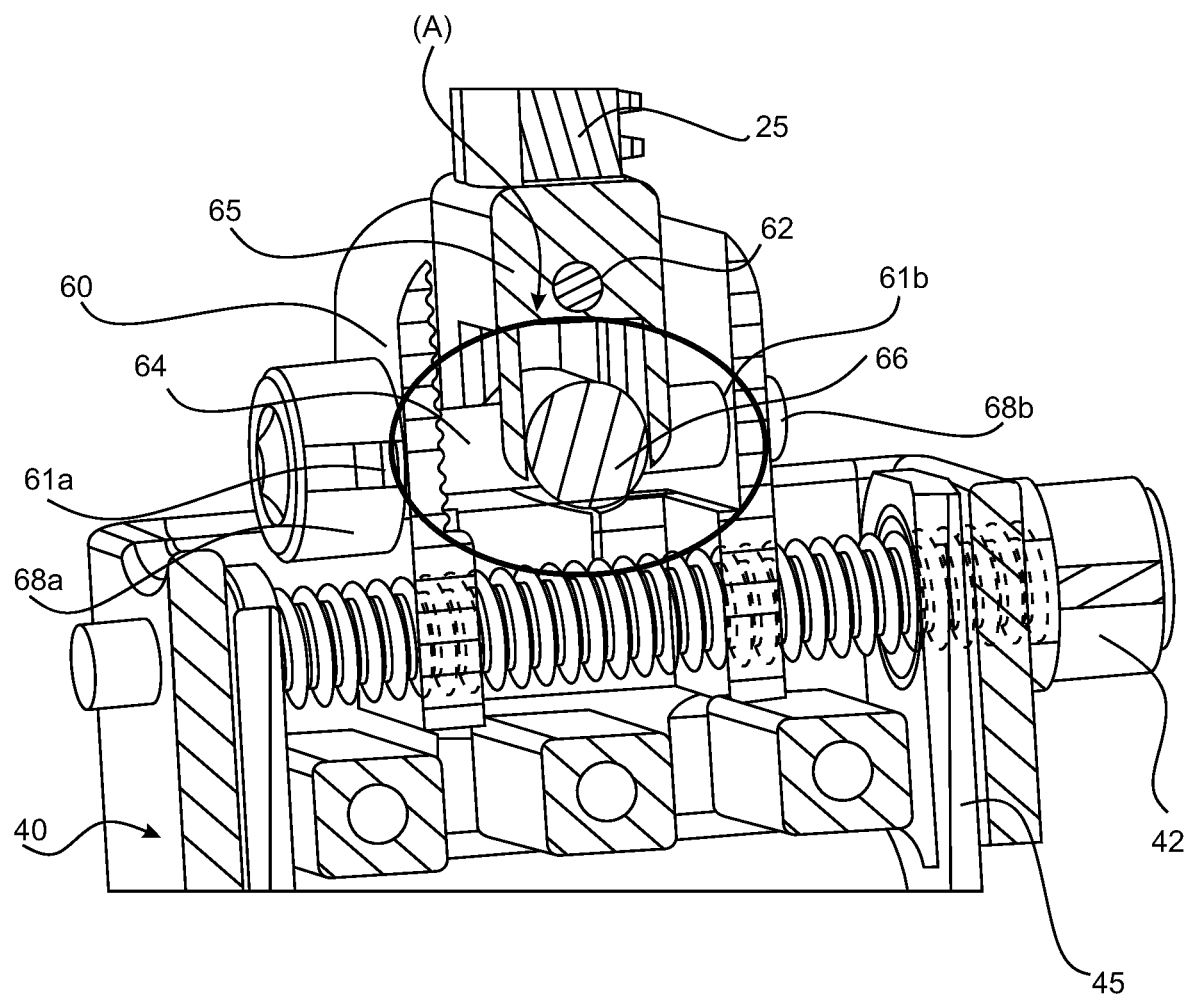
FIG. 5 is a cross-sectional view of the instrument in a medial section.
Figure 7:
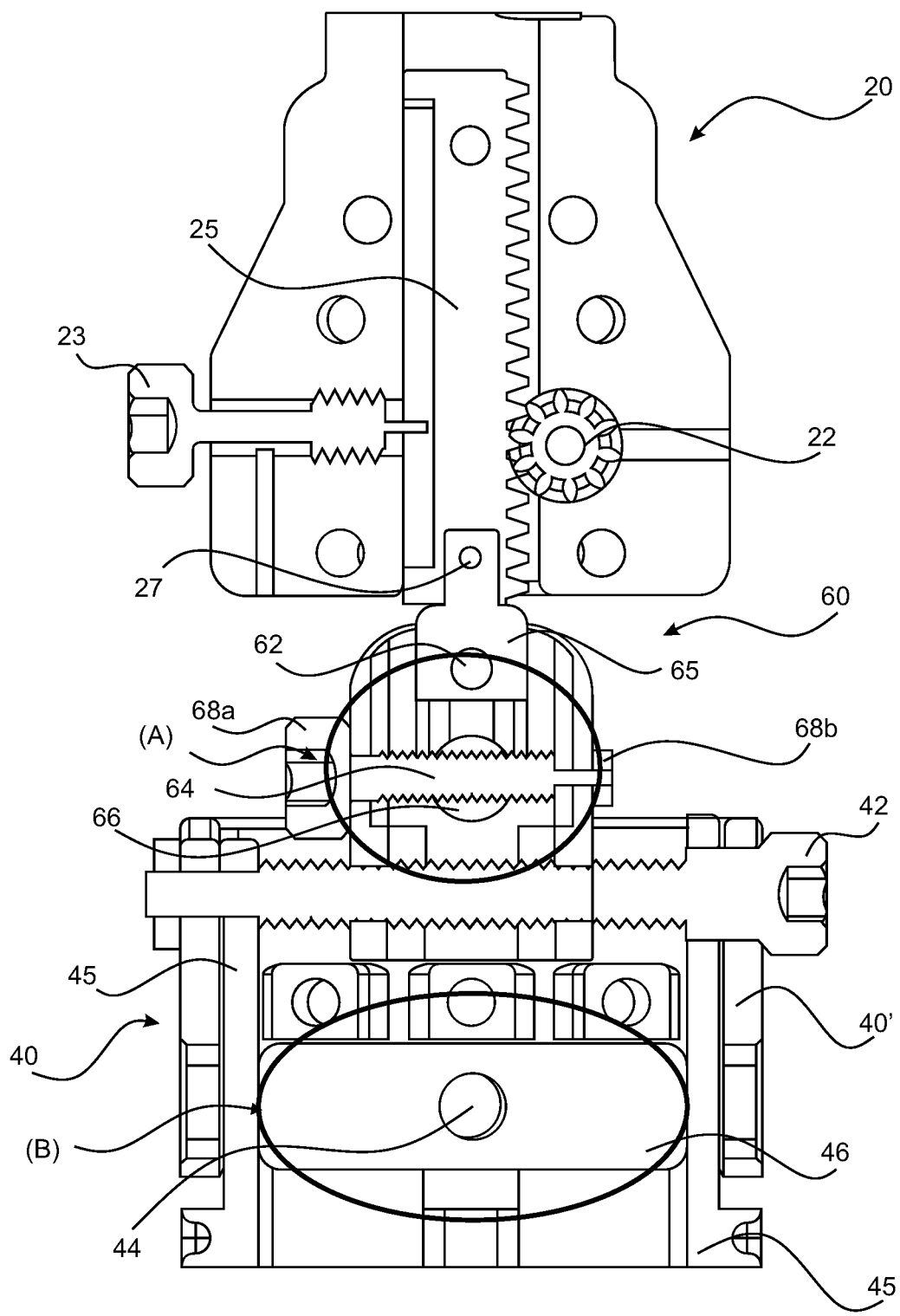
FIG. 7 is another cross-sectional view of the instrument.
Figure 8:
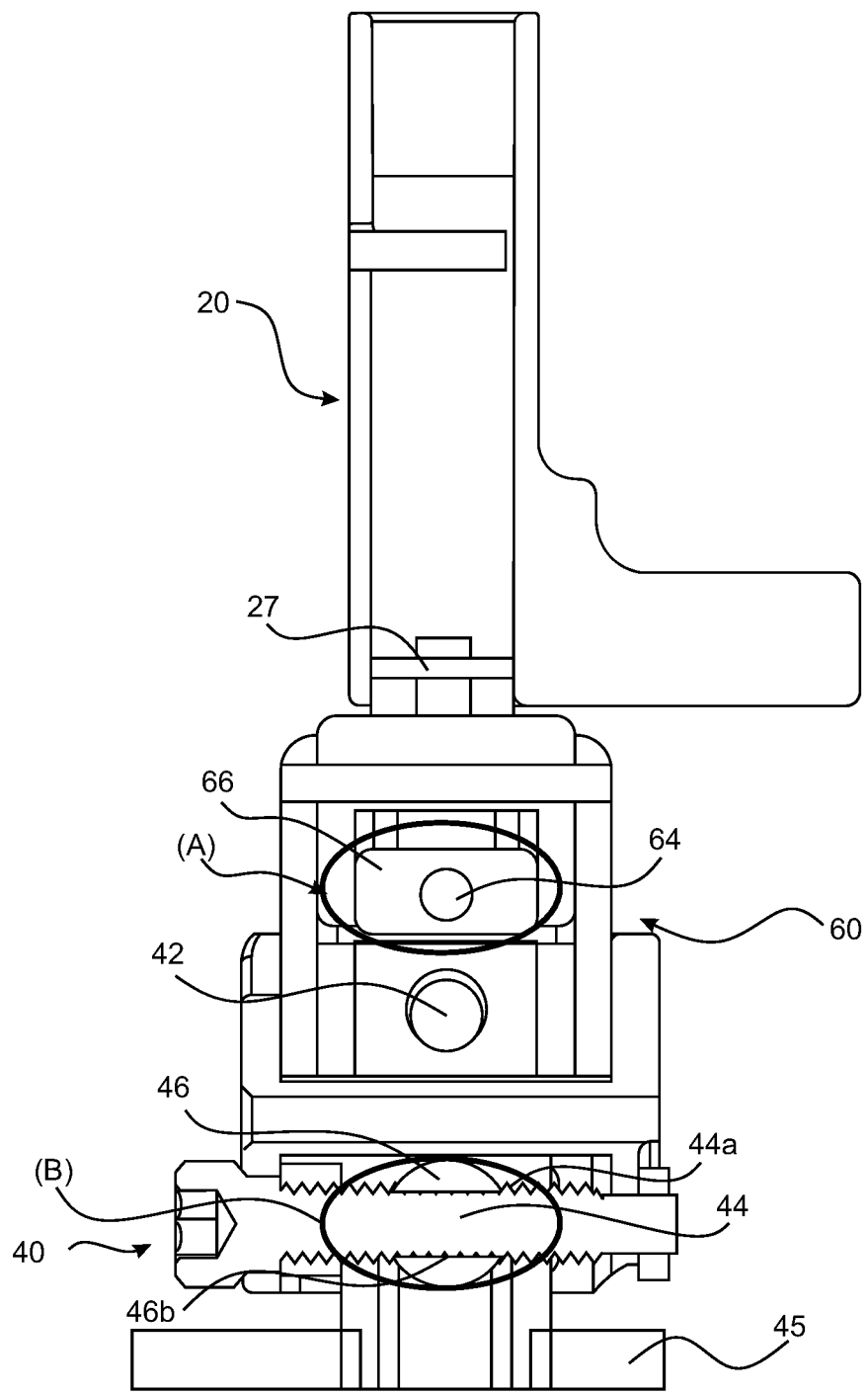
FIG. 8 is another cross-sectional view of the instrument.

As shown in FIGS. 4 and 5, the height adjustment assembly 22 also includes a shaft 25 that is connected to a linkage block 65. The shaft 25 is adjustable by engaging the height adjustment assembly 22, which is illustrated as a gear or screw in FIG. 4. As shown in FIGS. 7 and 8, a pin 27 is provided that connects the shaft 25 to the linkage block 65.

The proximal housing 20 is pivotally attached to the intermediate housing 60. In one embodiment, as shown in FIG. 4, a pin 62 provides a pivoting arrangement between the proximal housing 20 and the intermediate housing 60. The pin 62 provides an axis of revolution between the angle adjustment of the proximal housing 20 relative to the intermediate housing 60.

As shown at a high level in FIG. 2, the adjustment assembly 10 generally provides at least two linkage systems A, B. The linkage systems A, B are configured to provide angular adjustment in two different directions. In one embodiment, the two different directions are oriented perpendicular or 90 degrees relative to each other. A first angular adjustment shaft 64 is provided for the first linkage system A, and a second angular adjustment shaft 44 is provided for the second linkage system B. Specific details for the shafts 44, 64 and the other components engaged by the shafts 44, 64 are described in detail herein. However, the scope of this disclosure covers any type of interface arrangement that provides for a manually adjustable feature (i.e. the shafts 44, 64) and the ability to apply an impulse or action to the shaft such that the adjustment assembly 10 is adjusted in two directions. Various features of the threadings, the linkage shafts, etc. can be modified or omitted such that the same resulting angulation is achieved. In other words, one of ordinary skill in the art would understand that modifications to the linkage systems A, B can be implemented to achieve the same result of having an adjustment assembly 10 with at least two angulation adjustment features.

Generally, as the first angular adjustment shaft 64 is engaged or actuated (i.e. rotated), then an articulation angle between the proximal housing 20 and the distal housing 40 is adjusted. As shown in FIG. 2, as the first angular adjustment shaft 64 is actuated, the proximal housing 20 or the distal housing 40 will be pivoted in the coronal plane (X). As shown in FIG. 2, as the second angular adjustment shaft 44 is actuated, then another articulation angle between the proximal housing 20 and the distal housing 40 is adjusted, and the proximal housing 20 or the distal housing 40 will be pivoted in the sagittal plane (Y). Generally, the proximal housing 20 will be fixed to a patient during this adjustment stage, and therefore the distal housing 40 generally will be the mobile component that is driven during these adjustments. However, one of ordinary skill in the art would understand that relative positions of either housing 20, 40 can be adjusted.

The first angular adjustment shaft 64 is included with the intermediate housing 60. As used herein, the term angular adjustment shaft can refer to any screw, gear, bolt, threaded rod, etc. that is configured to be actuated to adjust an angular position between two components. The first angular adjustment shaft 64 is configured to be actuated, e.g. by a surgeon possibly using a tool, which adjusts a relative angle between the proximal housing 20 and the distal housing 40. In one aspect, the adjustment carried out by the first angular adjustment shaft 64 is completely independent of any height adjustment between the proximal housing 20 and the distal housing 40.

As shown in FIG. 2, a shaft 42 extends laterally though the distal housing 40. This shaft 42 generally connects the distal housing 40 to the intermediate housing 60. The shaft 42 also links a carriage 45 of the distal housing 40 to the intermediate housing 60. As shown in FIG. 7, the shaft 42 includes a smooth bearing surface in a region of the linkage 45, and an outer housing 40' of the distal housing 40. The shaft 42 includes threading to connect with the intermediate housing 60. The shaft 42 allows for pivoting or rotational movement between the distal housing 40 and the intermediate housing 60 due to the shaft 42 lacking any threading in an area of connection with the distal housing 40 or an outer housing 40' of the distal housing 40. The shaft 42 can include an enlarged head and/or locking washers on its axial ends to retain the shaft relative to the distal housing 40.

As shown in FIG. 2, a secondary instrument 5 can be provided. This secondary instrument 5 is shown as a guide tool that is configured to assist surgeons with drilling, cutting, inserting, and other actions associated with performing joint replacement surgeries. For example, the secondary instrument 5 can aid surgeons with fixing guide wires into a patient's bones. The secondary instrument 5 can be fixed to the distal housing 40 or the carriage 45 within the distal housing 40. The angular adjustments disclosed herein are primarily intended to adjust a relative position of the secondary instrument 5 relative to a patient's anatomy.

FIG. 4 illustrates a cross-sectional view of the adjustment assembly 10. The linkage block 65 pivots about the pin 62. The linkage block 65 houses a first linkage shaft 66 and generally positions the first linkage shaft 66 relative to the first angular adjustment shaft 64. The linkage shaft 66 is connected to the threading of the first angular adjustment shaft 64, such that the linkage shaft 66 essentially floats within the linkage block 65, and the linkage shaft 66 pushes the linkage block 65 in either direction when the first angular adjustment shaft 64 is rotated. In one aspect, the first linkage shaft 66 is constrained along two axes with respect to the linkage block 65. As the angular adjustment shaft 64 is rotated, the threaded region of the linkage shaft 66 moves along the axis of the threads of the angular adjustment shaft 64 thereby pushing the linkage block 65 along this axis and thereby causing the linkage block 65 to rotate about the pin 62.

As shown in FIG. 4, the linkage block 65 is fixed relative to the proximal housing 20. In one embodiment, the linkage block 65 can be formed integrally with the proximal housing 20. In another embodiment, the linkage block 65 can be fixed to the proximal housing 20 via other attachment configurations.

The first angular adjustment shaft 64 extends through openings 61a, 61b formed in the intermediate housing 60. The first linkage shaft 66 extends perpendicular to the first angular adjustment shaft 64.

Figure 6A:
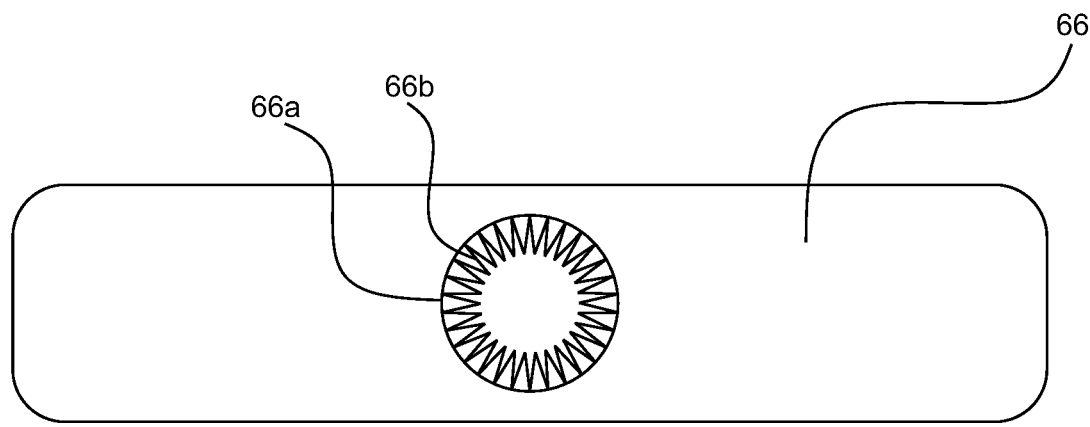
FIG. 6A illustrates features of a first linkage shaft.
Figure 6B:
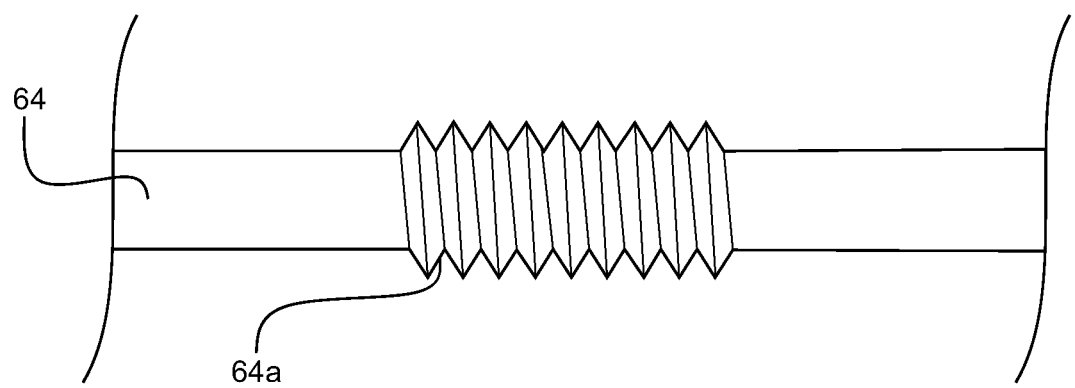
FIG. 6B illustrates features of a first angular adjustment shaft.

FIGS. 6A and 6B are simplified drawings to specifically only illustrate portions of the first linkage shaft 66 and the first angular adjustment shaft 64. As shown in FIG. 6A, in one embodiment the first linkage shaft 66 has a first threading 66b defined in a transversal opening 66a of the linkage shaft 66. For example, the first linkage shaft 66 can include a female threading that is oriented perpendicular relative to the longitudinal axis of the first linkage shaft 66. In another embodiment, the first linkage shaft 66 can include male threading or any other type of threading. The first angular adjustment shaft 64 extends perpendicular relative to the first linkage shaft 66 and inside the opening 66a of the first linkage shaft 66. As shown in FIG. 6B, the first angular adjustment shaft 64 includes a second threading 64a that is configured to mate with the first threading 66b on the first linkage shaft 66.

The first angular adjustment shaft 64 is configured to be rotated, and the first angular adjustment shaft 64 is fixed in a longitudinal or axial direction (i.e. the first angular adjustment shaft 64 is fixed in the left-right direction in FIG. 5 but is rotatable). To fix the first angular adjustment shaft 64, locking components 68a, 68b are provided. The locking components 68a, 68b can be formed integrally with the first angular adjustment shaft 64 or may be separately formed and then attached to the first angular adjustment shaft 64. As shown in FIG. 5, a first locking component 68a can be provided as an enlarged head of collar of the first angular adjustment shaft 64. A second locking component 68b can be provided as a washer that is fixed (e.g. welded) to an end of the first angular adjustment shaft 64.

In terms of operation, when the first angular adjustment shaft 64 is rotated, i.e. when a surgeon uses a tool to rotate a head or end formed on the first angular adjustment shaft 64, then the first angular adjustment shaft 64 rotates about its longitudinal axis in a linearly fixed orientation due to the locking components 68a, 68b. As a result of this rotation and the threadings 64a, 66b engaging with each other, the first linkage shaft 66, which is constrained to linear motion is driven along the first angular adjustment shaft 64. In one aspect, the first linkage shaft 66 is constrained by the position of its locking components 68a and 68b with respect to a length of the intermediate housing 60 through which the first linkage shaft 66 sits. In other words, the first linkage shaft 66 basically rides along the first angular adjustment shaft 64 as the first angular adjustment shaft 64 is rotated. The linear motion of the first linkage shaft 66 drives the linkage block 65 along the longitudinal axis of the first angular adjustment shaft 64.

Continuing with FIGS. 3A and 3B, various degrees of angular adjustment are illustrated. As shown in the figures, a tool 80 can be provided to manually engage the first angular adjustment shaft 64. The tool 80 can include any instrument, including handheld tools, e.g. a screwdriver, which is adapted to engage a surface of the first angular adjustment shaft 64 and impart rotational motion, i.e. twisting or turning motion, onto the first angular adjustment shaft 64. FIGS. 3A and 3B illustrate that the angle can be adjusted in two directions. The same tool 80 can be configured to engage both the first angular adjustment shaft 64 and the second angular adjustment shaft 44.

Figure 3C:
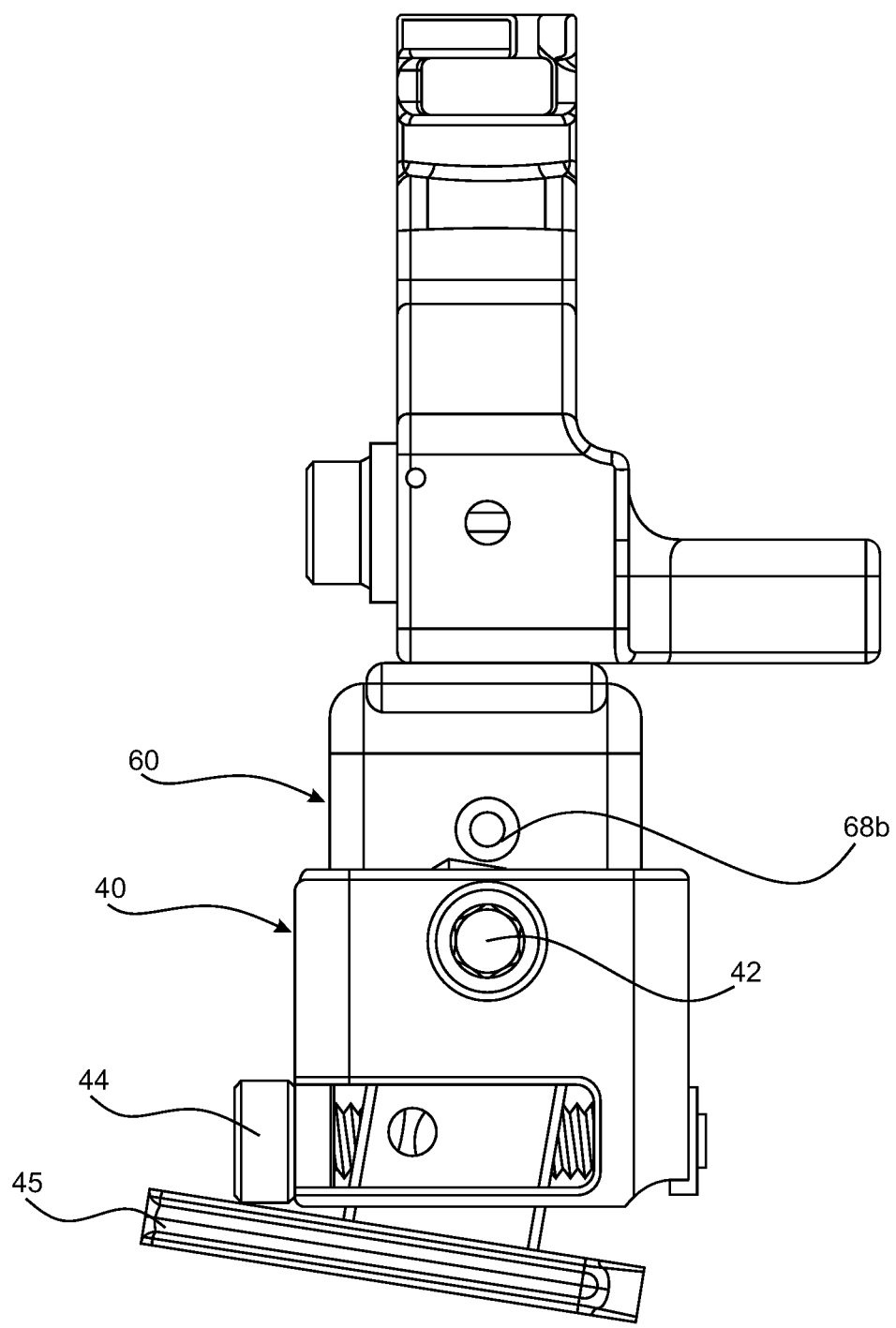
FIG. 3C is a side view of the instrument during adjustment in a first direction using a second linkage.

As shown in the drawings, the adjustment assembly 10 provides varus-valgus adjustment, i.e. adjustment in the coronal plane. For example, rotating the tool 80 clockwise can provide varus adjustment and rotating the tool 80 counter-clockwise can provide valgus adjustment, or vice versa. FIG. 3A shows an adjustment angle θ1, which can correspond to 15 degrees, and FIG. 3B shows an adjustment angle θ2, which can correspond to 15 degrees. The definition of varus and valgus is with respect to the patient's left or right extremity. As shown in FIG. 3A and FIG. 3B, the secondary instrument 5 is configured for a patient's right foot and therefore FIG. 3A shows a varus adjustment relative to the neutral position and FIG. 3B shows a valgus adjustment relative to the neutral position. Although the adjustment angles are not specifically annotated in FIGS. 3C-3E, the same range of adjustment can be provided using the other linkage and adjustment assembly.

Figure 3D:
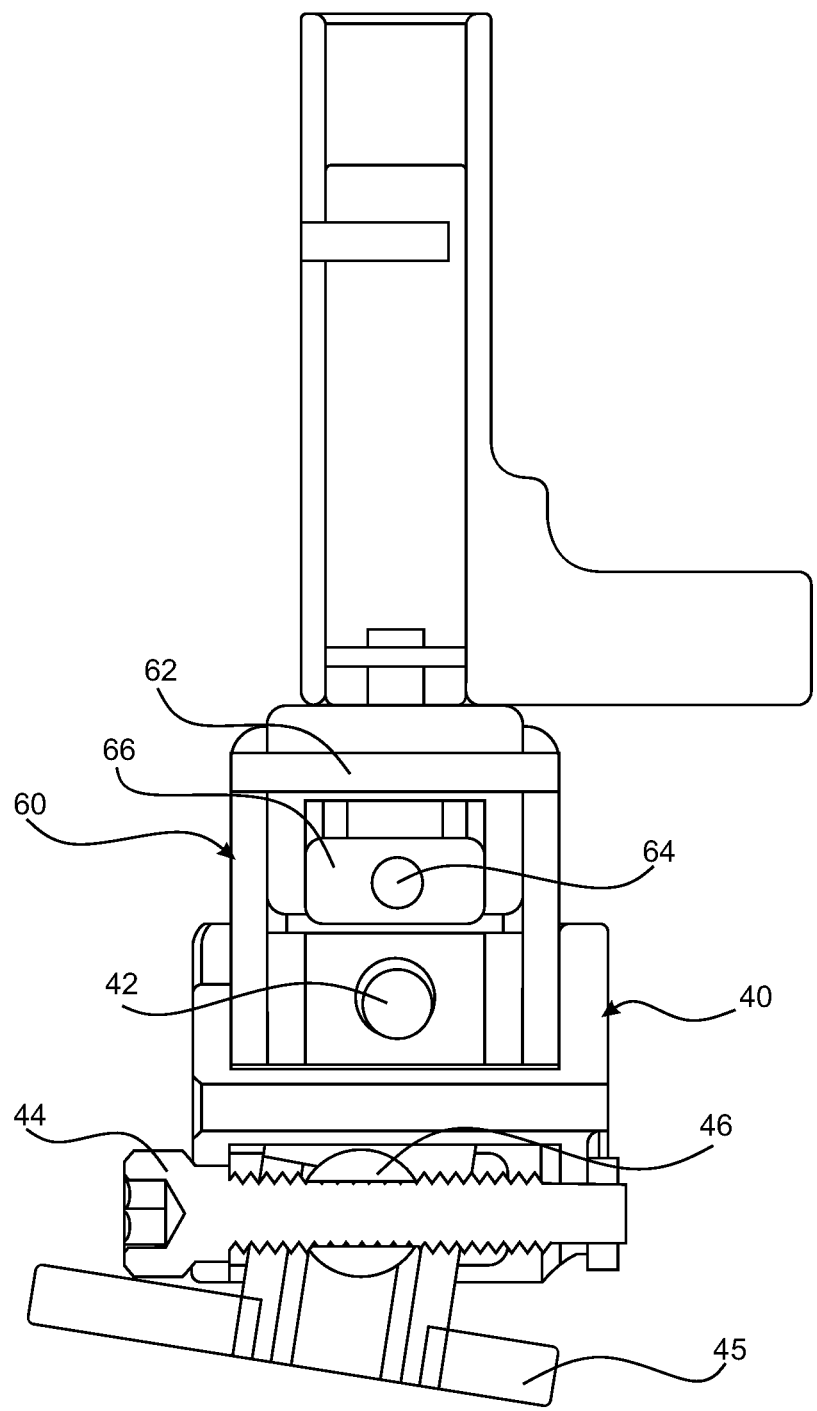
FIG. 3D is a side cross-sectional view of the instrument during adjustment in the first direction using the second linkage.

A second angular adjustment shaft 44 is provided, which functions according to the same mechanisms and features described above with respect to the first angular adjustment shaft 64. As shown in FIGS. 3D and 5, the carriage 45 is provided in the distal housing 40 (i.e. within the outer housing 40' of the distal housing 40), and the carriage 45 pivots about the shaft 42 when the second angular adjustment shaft 44 is actuated. A second linkage shaft 46 is constrained along two axes with respect to the carriage 45. The second linkage shaft 46 can rotate about its long axis (which is perpendicular to its threaded axis) and move up and down with respect to the carriage 45. As the second angular adjustment shaft 44 is rotated, the threaded region of the second linkage shaft 46 moves along the axis of the threads of the second angular adjustment shaft 44 thereby pushing the carriage 45 along this axis and thereby causing the carriage 45 to rotate about the shaft 42.

Figure 3E:
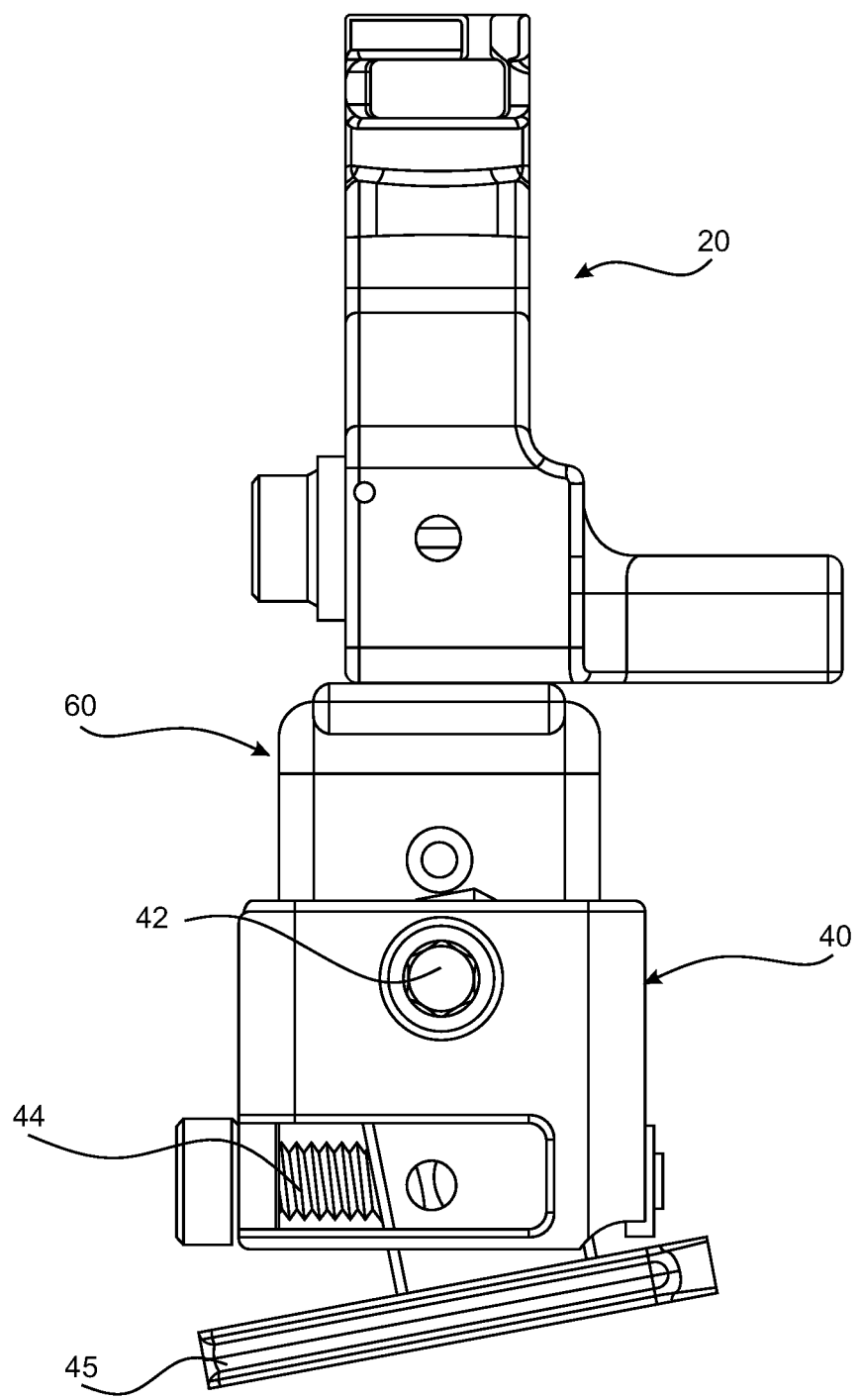
FIG. 3E is a side view of the instrument during adjustment in a second direction using the second linkage.

Actuation of the second angular adjustment shaft 44 generally converts rotational input applied to the second angular adjustment shaft 44 into linear motion imparted onto the second linkage shaft 46. The general function and operation of the second linkage B/angular adjustment shaft 44 is similar to the first linkage A/angular adjustment shaft 64. As shown in the drawings, there is threading on both the second angular adjustment shaft 44 and the second linkage shaft 46 to provide a driving engagement between the two components. The second linkage shaft 46 is housed within the carriage 45. The second linkage shaft 46 is driven linearly along a longitudinal axis of the second linkage shaft 46. The carriage 45 and the distal housing 40 are linked to each other about an axis of the shaft 42 but are otherwise mobile relative to each other and can be adjusted. Accordingly, any linear translation of motion between the second angular adjustment shaft 44 and the second linkage shaft 46 modifies a relative angular position between the carriage 45 and the distal housing 40. FIGS. 3C-3E illustrate various states of these adjustments. The threadings 44a, 46b on the second linkage shaft 46 and the second angular adjustment shaft 44 are not specifically described in more detail but are otherwise similar to the threadings 64a, 66b.

In one embodiment, the adjustments by the linkage systems A, B allow the surgeon to adjust the opening angle (commonly referred to as "slope") of the instrument relative to the patient's anatomy. In one embodiment, the adjustments by the linkage systems A, B allow the surgeon to adjust the varus-valgus angle of the instrument relative to the patient's anatomy. In one embodiment, both of the linkage systems A, B can utilize a screw type feature that actuates the instrument, causing it rotate about a fixed point, thereby adjusting the relative angle between the instrument and the bone. In one embodiment, these adjustments can be made between +45° and −45° from a line perpendicular to the long axis of the tibial instrument. In other words, linkage systems A, B allow a surgeon to precisely and accurately adjust a relative position of the secondary instrument 5 (i.e. a cutting guide or tool) relative to the patient. The linkage systems A, B permit adjustments and reduce the likelihood of misalignment and improves a surgeon's ability to precisely select the angle most appropriate for the patient.

Figure 9B:
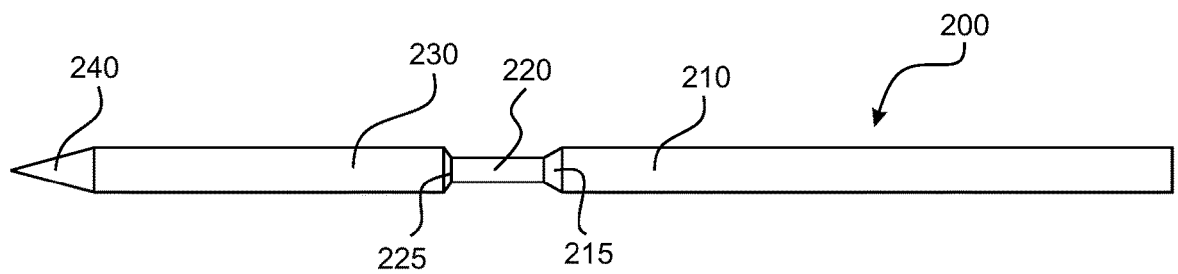
FIG. 9B is a side view of a guide wire according to another embodiment.
Figure 9B:
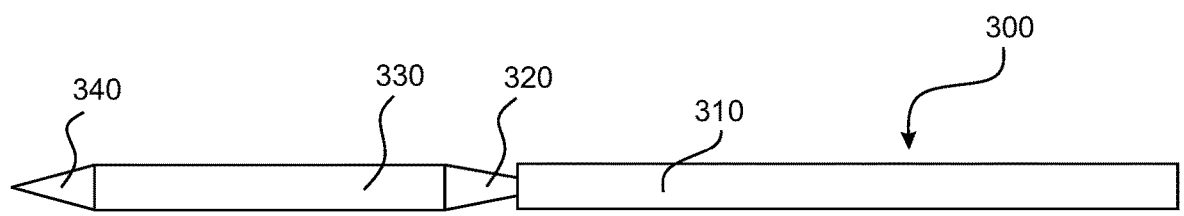

As shown in FIGS. 9A and 9B, a guide wire 200, 300 is provided that includes a varying profile. The modified profile of the guide wires 200, 300 provides for a more reliable sever point or breaking point due to the reduced thickness in the transition regions. This configuration helps reduce the cut or broken ends of the guide wires 200, 300 from interfering with any openings or holes on instruments as various instruments are placed onto the severed guide wires 200, 300. A depth or end point of the transition regions of the guide wires 200, 300 are selected such that the transition regions will remain outside of a patient's anatomy during a typical surgery. For example, the depth or end point of the transition regions is between 0.25 inches and 3.0 inches. In another embodiment, the transition regions are positioned at least ¼-⅓ of a total length of the guide wires 200, 300 away from the tips.

As shown in FIG. 9A, the guide wire 200 includes a proximal region 210, a transition region 220, a distal region 230, and a tip 240. As shown in FIG. 9A, the guide wire 200 has a generally cylindrical profile. A length of the guide wire 200 can vary on the particular size requirements dictated by the type of surgery and depth that is required for the guide wire 200. In a direction from the proximal region 210 to the transition region 220, a first connection portion 215 is provided. The first connection portion 215 has a tapered profile. A length of the transition region 220 is shorter than the proximal region 210 and the distal region 230. The transition region 220 is connected to the distal region 230 with a second connection portion 225. As shown in FIG. 9A, the second connection portion 225 has a shorter tapered profile than the profile of the first connection portion 215. The distal region 230 has a cylindrical profile, similar to the profile of the proximal region 210. A length of the distal region 230 is less than a length of the proximal region 210 in one embodiment. A thickness or diameter of the distal region 230 is different than a thickness or diameter of the transition region 220 in one embodiment. As shown in the drawings, the distal region 230 is thicker than the transition region 220. In one embodiment, a least a portion of an outermost diameter of the transition region 220 is less than 75% of a diameter of the distal region 230. The tip 240 is defined at an axial end of the distal region 230 opposite from the second connection portion 225. The tip 240 includes a point, that can have a tapered or trocar profile.

As shown in FIG. 9B, the guide wire 300 includes a proximal region 310, a transition region 320, a distal region 330, and a tip 340. The proximal region 310 is similar to the proximal region 210 and includes a generally cylindrical profile. The transition region 320 that tapers from a larger end (connected to the distal region 330) to a smaller end (connected to the proximal region 310). The distal region 330 has a generally cylindrical profile, similar to the distal region 230. The distal region 330 terminates with the tip 340. A taper of the transition region 320 is similar to the taper of the tip 340 but in an opposite direction or orientation. In one embodiment, a taper of the tip 340 is greater than a taper of the transition region 320.

The guide wires 200, 300 can be used in the adjustment assembly 10 disclosed herein and can be inserted into the guide wire openings on various parts of the adjustment assembly 10.

Figure 10A:
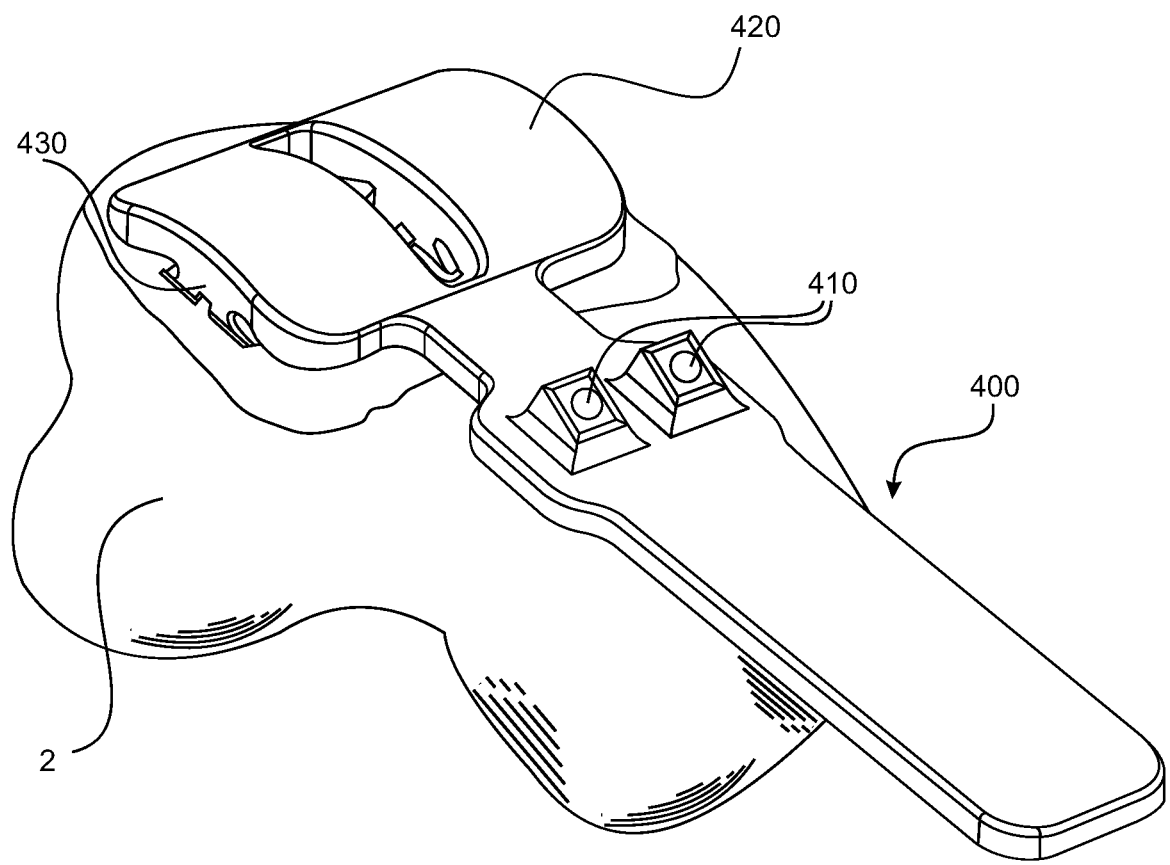
FIGS. 10A-10D illustrate various steps of using the guide wires of either FIG. 9A or 9B.

In use, a surgeon would align a first surgical instrument 400 onto a patient's talus 2 (as shown in FIG. 10A) and insert at least one guide wire 200 into a guide hole 410 in the first surgical instrument 400. Once the guide wire 200 is inserted into a patient's anatomy, at least a portion of the transition region 220 is configured to remain outside of a patient's bone, i.e. talus 2. Regarding the first instrument 400, this instrument 400 can include the guide holes 410, a sizing surface 420 shaped to approximate a size of an implant, and other profile features 430 that are shaped to approximate other features on the implant.

Figure 10B:
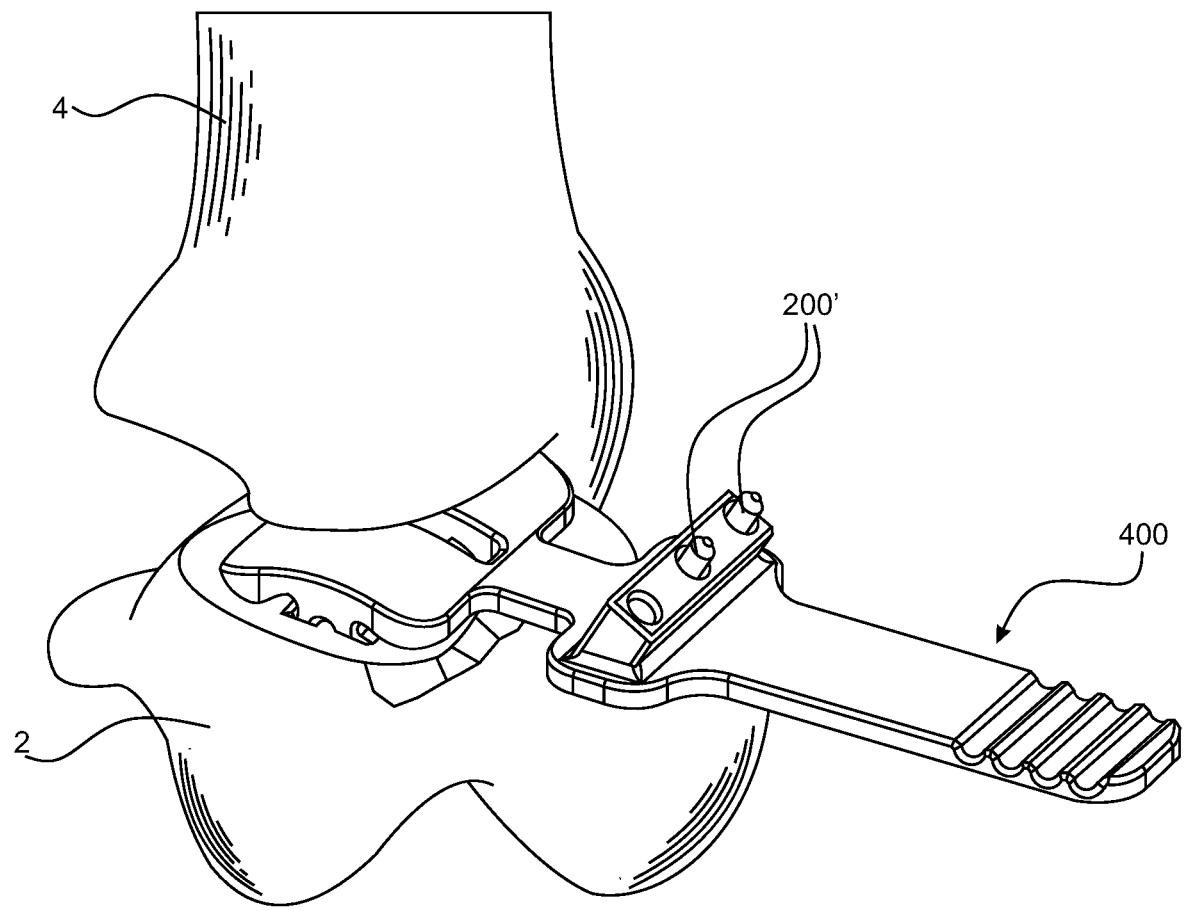
Figure 10C:
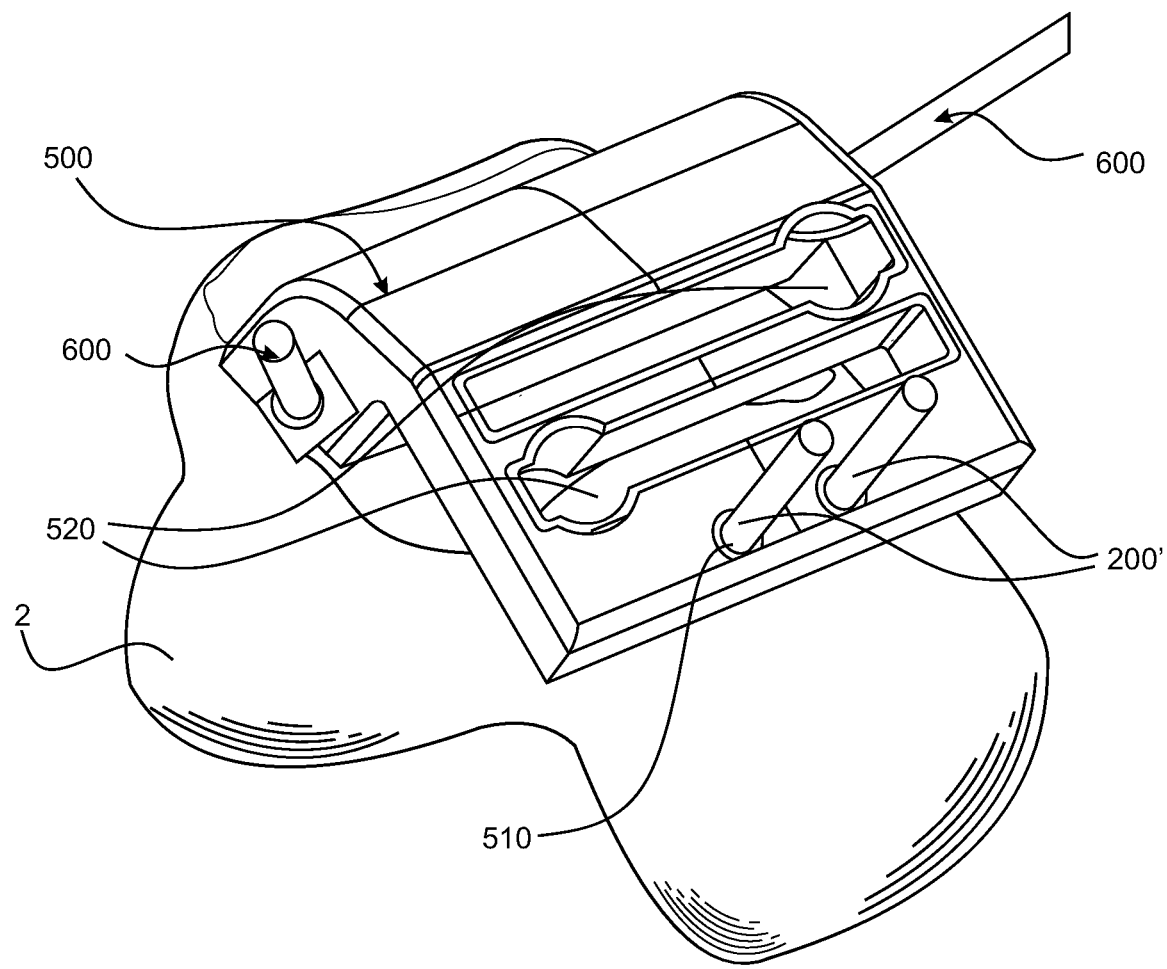
Figure 10D:
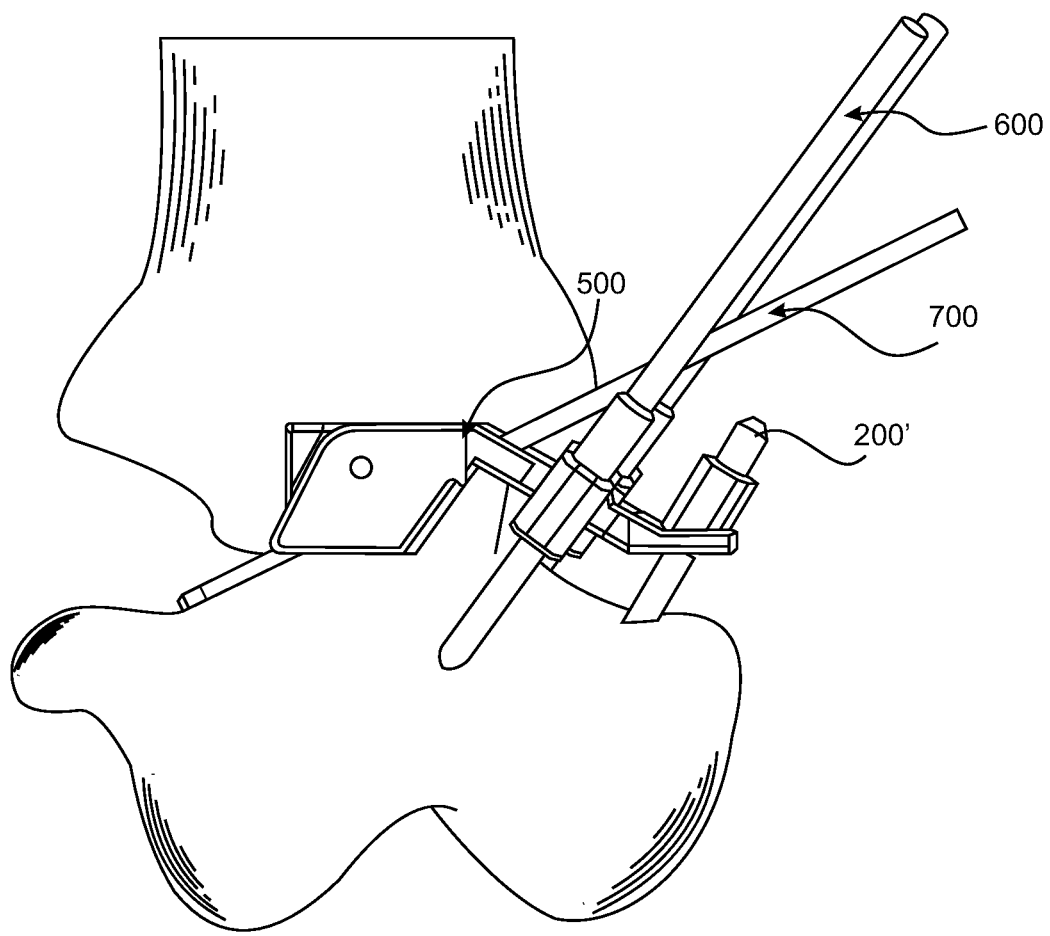

The surgeon cuts or severs the guide wire 200 in the transition region 220, as shown in FIG. 10B. After removing the first surgical instrument 400, the surgeon then positions a second surgical instrument 500 with respect to a remaining portion of the now severed guide wire 200', as shown in FIG. 10C. The second surgical instrument 500 includes guide holes 510 for the severed guide wires 200' and at least one opening, aperture, slot, or hole 520 dimensioned or configured to receive or accept a cutting device 700 (shown in FIG. 10D). The cutting device 700 is generally configured to remove a portion of a patient's talus 2.

An additional element 600 can be provided to further stabilize the second instrument 500. The additional element 600 can include a tool, guide wire, instrument, bone screw, or other type of element capable of fixing a position of the second surgical instrument 500.

In another embodiment, the method of using the guide wire 200 can include inserting the guide wire 200 into a guide hole 410 of a first instrument 400, removing the first instrument 400, positioning a second instrument 500 with respect to the guide wire 200, and then severing the guide wire 200 in the transition region 220. In other words, the sequence of removing the instruments and cutting or severing the guide wire 200 can vary.

Features of the first and second instruments 400, 500 can vary. The guide wire 200 has a profile that prevents the guide wire 200 from having a splayed or deformed severed end such that the guide holes 410, 510 of the instruments 400, 500 are incapable of sliding over the severed guide wires 200'.

One of ordinary skill in the art would understand from this disclosure that any one or more of the embodiments can be used in connection with any one or more of the steps described herein.

Having thus described the present invention in detail, it is to be appreciated and will be apparent to those skilled in the art that many physical changes, only a few of which are exemplified in the detailed description of the invention, could be made without altering the inventive concepts and principles embodied therein.

It is also to be appreciated that numerous embodiments incorporating only part of the preferred embodiment are possible which do not alter, with respect to those parts, the inventive concepts and principles embodied therein.

The present embodiment and optional configurations are therefore to be considered in all respects as exemplary and/or illustrative and not restrictive, the scope of the invention being indicated by the appended claims rather than by the foregoing description, and all alternate embodiments and changes to this embodiment which come within the meaning and range of equivalency of said claims are therefore to be embraced therein.

The invention claimed is:

1. An alignment assembly for adjusting a position of a guide tool relative to a patient, the alignment assembly comprising:
    a proximal housing;
    a distal housing configured to be connected to the guide tool; and
    at least one linkage system configured to adjust a relative angle between the proximal housing and the distal housing, wherein the at least one linkage system includes a first linkage system and a second linkage system such that the first and second linkage systems are configured to provide angular adjustment in two different directions that are oriented 90 degrees relative to each other, and the first and second linkage systems each translate rotational input motion to linear output motion.

2. The alignment assembly of claim 1, wherein the distal housing includes a carriage configured to be connected to the guide tool, and the first linkage system adjusts a relative position of proximal housing to the distal housing in a coronal plane, and the second linkage system adjusts a relative position of the carriage to the distal housing in a sagittal plane.

3. The alignment assembly of claim 1, wherein the relative angle is adjusted between +75° and −75° from a line perpendicular to a longitudinal axis (X1) of the alignment assembly.

4. The alignment assembly of claim 1, further comprising an intermediate housing positioned between the proximal housing and the distal housing.

5. The alignment assembly of claim 4, wherein the first linkage system includes a first angular adjustment shaft extending through the intermediate housing, and the second linkage system includes a second angular adjustment shaft extending through the distal housing.

6. The alignment assembly of claim 5, wherein:
    the first angular adjustment shaft includes a first threading and extends through a first linkage shaft having a second threading configured to engage with the first threading, and rotational motion applied to the first angular adjustment shaft drives the first linkage shaft linearly along the first angular adjustment shaft such that distal housing and the proximal housing pivot relative to each other in a first direction, and
    the second angular adjustment shaft includes a third threading and extends through a second linkage shaft having a fourth threading configured to engage with the third threading, and rotational motion applied to the second angular adjustment shaft drives the second linkage shaft linearly along the second angular adjustment shaft such that the distal housing and a carriage of the distal housing pivot relative to each other in a second direction.

7. The alignment assembly of claim 6, further comprising a height adjustment assembly configured to adjust a relative height between the proximal housing and the distal housing.

8. The alignment assembly of claim 7, wherein the height adjustment assembly is positioned on the proximal housing.

9. The alignment assembly of claim 6, wherein a single tool is configured to engage the first angular adjustment shaft and the second angular adjustment shaft, and the single tool is configured to rotationally engage both the first angular adjustment shaft and the second angular adjustment shaft.

10. The alignment assembly of claim 6, further comprising a height adjustment assembly.

11. The alignment assembly of claim 1, wherein the proximal housing and the distal housing each include a plurality of guide wire openings.

12. The alignment assembly of claim 1, wherein the proximal housing remains stationary during adjustments by the at least one linkage system.

\* \* \* \* \*